United States Patent [19]
Dillenburg et al.

[11] Patent Number: 5,648,067
[45] Date of Patent: Jul. 15, 1997

[54] COSMETIC DEODORANT PREPARATION CONTAINING DI- OR TRIGLYCERIN ESTERS

[75] Inventors: Helmut Dillenburg; Gerald Jakobson, both of Rheinberg; Winfried Klein, Hamburg; Werner Siemanowski, Rheinberg; Karlheinz Uhlig, Krefeld; Florian Wolf, Hamburg, all of Germany

[73] Assignees: Beiersdorf Aktiengesellschaft, Hamburg; Solvay Fluor und Derivate GmbH, Hannover, both of Germany

[21] Appl. No.: 428,088

[22] PCT Filed: Oct. 9, 1993

[86] PCT No.: PCT/EP93/02767

§ 371 Date: Aug. 17, 1995

§ 102(e) Date: Aug. 17, 1995

[87] PCT Pub. No.: WO94/09753

PCT Pub. Date: May 11, 1994

[30] Foreign Application Priority Data

Nov. 3, 1992 [DE] Germany ............ 42 37 081.7

[51] Int. Cl.$^6$ ...................................... A61K 7/32
[52] U.S. Cl. ................. 424/65; 424/400; 424/401
[58] Field of Search .................. 424/65, 400, 401

[56] References Cited

U.S. PATENT DOCUMENTS 4,704,271  11/1987  Howrihan et al. ............... 424/66

*Primary Examiner*—Shelley A. Dodson
*Attorney, Agent, or Firm*—Sprung Horn Kramer & Woods

[57] ABSTRACT

Cosmetic deodorants, characterized by an active content of monocarboxylic acid esters of di- and/or triglycerol.

11 Claims, 1 Drawing Sheet

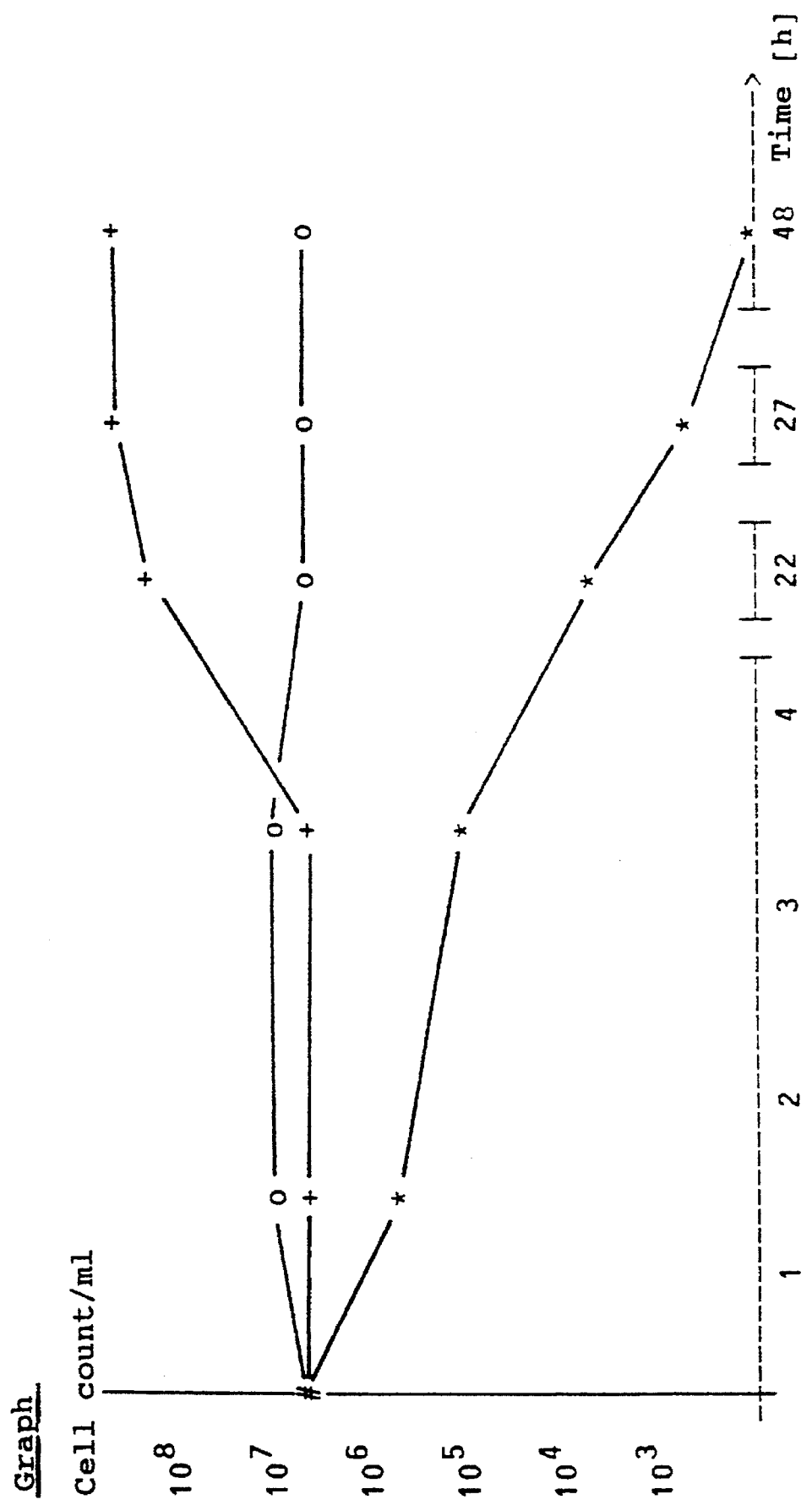

COSMETIC DEODORANT PREPARATION CONTAINING DI- OR TRIGLYCERIN ESTERS

The present invention relates to cosmetic deodorants. Such formulations are used to eliminate body odour which arises when fresh perspiration, which is in itself odourless, is decomposed by microorganisms. The commercially available cosmetic deodorants are based on various action principles.

In so-called antiperspirants, the formation of perspiration can be suppressed by astringents—chiefly aluminium salts, such as aluminium hydroxychloride (aluminium chlorohydrate). Apart from denaturing skin proteins, however, the substances used for this purpose intervene drastically in the thermal balance of the axillary region according to their dosage, and should at best be used in exceptional cases.

The bacterial flora on the skin can be reduced by the use of antimicrobial substances in cosmetic deodorants. In the ideal case, only the microorganisms which cause odour should be actively reduced here. In practice, however, it has been found that the entire microflora of the skin may be impaired.

The flow of perspiration itself is not affected thereby, and in the ideal case only the microbial decomposition of the perspiration is temporarily stopped.

The combination of astringents with antimicrobially active substances in one and the same composition is also customary. However, the disadvantages of the two classes of active compound cannot be eliminated completely by this route.

Finally, body odour can also be masked by fragrances, a method which least meets the aesthetic requirements of the consumer, since the mixture of body odour and perfume fragrance smells rather unpleasant.

Nevertheless, most cosmetic deodorants, as is the case with most cosmetics overall, are perfumed, even if they comprise deodorizing active compounds. Perfuming can also serve to increase the user acceptance of a cosmetic product, or to give a product a certain cachet.

However, perfuming of cosmetic formulations, in particular cosmetic deodorants, containing active compounds is not infrequently problematic, because active compounds and perfume constituents can occasionally react with one another and render each other inactive.

Deodorants should meet the following conditions:
1) They should cause a reliable deodorizing.
2) The natural biological processes of the skin should not be impaired by the deodorants.
3) The deodorants must be harmless in overdose or when otherwise not used as specified.
4) After repeated use, they should not become concentrated on the skin.
5) They should be easy to incorporate into customary cosmetic formulations.

Both liquid deodorants, for example aerosol sprays, roll-ons and the like, and solid formulations, for example deodorant sticks, powders, powder sprays, intimate cleansing compositions and the like, are known and customary.

The object of the present invention was thus to develop cosmetic deodorants which do not have the disadvantages of the prior art. In particular, the deodorants should largely preserve the microflora of the skin, but selectively reduce the number of microorganisms responsible for body odour.

It was furthermore an object of the invention to develop cosmetic deodorants which are distinguished by a good skin tolerability. Under no circumstances should the deodorizing active principles become concentrated on the skin.

Another object was to develop cosmetic deodorants which harmonize with the largest possible number of customary cosmetic auxiliaries and additives, in particular with the perfume constituents which are important precisely in formulations having a deodorizing or antiperspirant action.

Yet another object of the invention was to provide cosmetic deodorants which are active over a relatively long period of time, in particular of the order of at least half a day, without their action subsiding noticeably.

Finally, an object of the present invention was to develop deodorizing cosmetic principles which can be incorporated as universally as possible into the most diverse presentation forms of cosmetic deodorants without being limited to one or a few specific presentation forms.

Surprisingly, it has been found, and therein lies the achievement of all these objects, that cosmetic deodorants having an active content of monocarboxylic acid esters of di- and/or triglycerol remedy the disadvantages of the prior art.

It is indeed known that fatty acid esters of glycerol (that is to say of monoglycerol demonstrate a certain antimicrobial action. It is furthermore known to employ monoglycerol fatty acid esters, in particular glycerol monolaurate, in deodorizing cosmetics. Nevertheless, the action of these monoglycerol esters remains far behind that of the monocarboxylic acid esters according to the invention.

According to the invention, the di- and triglycerol units of the monocarboxylic acid esters according to the invention are in the form of linear, unbranched molecules, that is to say "monoglycerol molecules" etherified via the particular OH groups in the 1- or 3-position.

$$\overset{3}{H_2C}-\overset{2}{CH}-\overset{1}{CH_2} \quad \text{(glycerol = "monoglycerol")}$$
$$\,|\quad\,|\quad\,|$$
$$HO\;\;OH\;\;OH$$

A small content of cyclic di- or triglycerol units and glycerol molecules etherified via the OK groups in the 2-position can be tolerated. However, it is advantageous to keep such impurities as low as possible.

The monocarboxylic acid esters of diglycerol according to the invention are preferably monocarboxylic acid monoesters and are preferably characterized by the following structure (substitution positions shown):

$$\overset{3'}{H_2C}-\overset{2'}{CH}-\overset{1'}{CH_2}-O-\overset{3}{CH_2}-\overset{2}{CH}-\overset{1}{CH_2}-O-\overset{}{C}-R'$$
$$\,|\quad\,|\quad\quad\quad\quad\,|\quad\quad\quad\quad\,\|$$
$$HO\;\;OH\quad\quad\quad\;OH\quad\quad\quad\;O$$

wherein R' is a hydrocarbon radical, advantageously a branched or unbranched alkyl or alkenyl radical having 5 to 17C atoms.

The monocarboxylic acid esters of triglycerol according to the invention are preferably monocarboxylic acid monoesters and are preferably characterized by the following structure (substitution positions shown):

$$\overset{3''}{H_2C}-\overset{2''}{CH}-\overset{1''}{CH_2}-O-\overset{3'}{CH_2}-\overset{2'}{CH}-\overset{1'}{CH_2}-O-\overset{3}{CH_2}-\overset{2}{CH}-\overset{1}{CH_2}$$
$$\,|\quad\,|\quad\quad\quad\quad\,|\quad\quad\quad\quad\quad\quad\quad\,|\quad\,|$$
$$HO\;\;OH\quad\quad\quad\;O\quad\quad\quad\quad\quad\quad OH\;\;OH$$
$$\quad\quad\quad\quad\quad\quad\quad\;|$$
$$\quad\quad\quad\quad\quad\quad\;C=O$$
$$\quad\quad\quad\quad\quad\quad\quad\;|$$
$$\quad\quad\quad\quad\quad\quad\quad\;R''$$

wherein R" is a hydrocarbon radical, advantageously a branched or unbranched alkyl or alkenyl radical having 5 to 17C atoms.

The acids on which these esters are based are hexanoic acid (caproic acid) (R' or R"=–$C_5H_{11}$), heptanoic acid (oenanthic acid) (R' or R"=–$C_6H_{13}$), octanoic acid (caprylic acid) (R' or R"=–$C_7H_{15}$), nonanoic acid (pelargonic acid) (R' or R"=–$C_8H_{17}$), decanoic acid (capric acid) (R' or R"=–$C_9H_{19}$), undecanoic acid (R' or R"=–$C_{10}H_{20}$), 10-undecenoic (undecylenic acid) (R' or R"=–$C_{10}H_{21}$), acid dodecanoic acid (lauric acid) (R' or R"=–$C_{11}H_{23}$), tridecanoic acid (R' or R"=–$C_{12}H_{25}$), tetradecanoic acid (myristic acid) (R' or R"=–$C_{13}H_{27}$), pentadecanoic acid (R' or R"=–$C_{14}H_{29}$), hexadecanoic acid (palmitic acid) (R' or R"=–$C_{15}H_{31}$), heptadecanoic acid (margaric acid) (R' or R"=–$C_{16}H_{33}$), octadecanoic acid (stearic acid) (R' or R"=–$C_{17}H_{35}$).

R' and R" are particularly favourably chosen from the group consisting of unbranched alkyl radicals having odd C numbers, in particular having 9, 11 and 13C atoms.

The esters of diglycerol are generally preferable to those of triglycerol.

Esters which are especially favourable are
diglycerol monocaprate (DMC) R'=9
triglycerol monolaurate (TML) R"=11
diglycerol monolaurate (DML) R'=11
triglycerol monomyristate (TMM) R"=13.

Diglycerol monocaprate (DMC) has proved to be the preferred monocarboxylic acid ester according to the invention.

The diglycerol mono-fatty acid esters according to the invention are preferably esterified in the 1-position and the triglycerol mono-fatty acid esters according to the invention are preferably esterified in the 2'-position.

According to an advantageous embodiment of the present invention, an additional content of di- or triglycerol esterified in other positions, and also, where appropriate, a content of the various diesters of di- or triglycerol, are used.

Those monocarboxylic acid esters which are obtainable by a process such as is described in DE-A 38 18 293 are particularly advantageous.

The diglycerol esters, which are distinguished by two centres of asymmetry, and the triglycerol esters, which are distinguished by three centres of asymmetry, are active according to the invention in all of their configurations. The diglycerol esters have four stereoisomers and the triglycerol esters have eight stereoisomers.

In the diglycerol esters, the 2- and the 2'-positions are centres of asymmetry. The 2S2'S, the 2R2'S, the 2S2'R and the 2R2'R configurations are active according to the invention and equally of advantage.

The 2-, the 2'- and the 2"-positions are centres of asymmetry in the triglycerol esters. The 2S2'S2"S, the 2R2'S2"S, the 2S2'R2"S, the 2R2'R2"S, the 2S2'S2"R, the 2R2'S2"R, the 2S2'R2"R and the 2R2'R2"R configurations are active according to the invention and equally of advantage.

It has proved favourable to use racemic mixtures of the stereoisomers.

According to an advantageous embodiment of the present invention, mixtures of one or more monocarboxylic acid esters of diglycerol with one or more monocarboxylic acid esters of triglycerol are used.

According to another advantageous embodiment of the present invention, one or more monocarboxylic acid esters of diglycerol and/or one or more monocarboxylic acid esters of triglycerol are employed in combination with other active compounds (substitute active compounds), auxiliaries, extenders and/or additives customary in cosmetics.

The extenders and/or substitute active compounds are then advantageously present in a concentration of up to 50 parts by weight, preferably up to 35 parts by weight, per 100 parts by weight of the total amount, which is composed of the monocarboxylic acid ester or monocarboxylic acid esters of diglycerol and/or of triglycerol and these substitute active compounds and/or extenders.

According to another advantageous embodiment of the present invention, one or more monocarboxylic acid esters of diglycerol and/or one or more monocarboxylic acid esters of triglycerol are employed in combination with other deodorizing substances or substances which inhibit the growth of bacteria or destroy bacteria.

According to yet another advantageous embodiment of the present invention, one or more monocarboxylic acid esters of diglycerol and/or one or more monocarboxylic acid esters of triglycerol are employed in combination with monocarboxylic acid esters of glycerol (that is to say "monoglycerol"). In this case, these monocarboxylic acid esters of glycerol assume the role of extenders and/or substitute active compounds and are preferably employed in a concentration of up to 50 parts by weight, preferably up to 35 parts by weight, per 100 parts by weight of the total amount, which is composed of the monocarboxylic acid ester or the monocarboxylic acid esters of diglycerol and/or of triglycerol and these monocarboxylic acid esters of glycerol.

Such monocarboxylic acid esters of glycerol are favourably characterized by a structure as follows:

$$H_2C-CH-CH_2-O-\underset{\underset{O}{\|}}{C}-R'''$$
$$\phantom{H_2C-}\underset{HO}{|}\phantom{-}\underset{OH}{|}$$

wherein R''' is a hydrocarbon radical, advantageously a branched or unbranched alkyl or alkenyl radical having 5 to 17C atoms.

The deodorizing action of the esters according to the invention is primarily based on their selective toxicity to Gram-positive bacteria, in particular coryne-form bacteria. These are regarded as being chiefly responsible for the decomposition of apocrine perspiration. The esters according to the invention furthermore have a good action against Staphylococci.

Since the esters according to the invention at the same time are completely harmless to humans and other warm-blooded animals, they are ideally suitable for use in cosmetic deodorants.

The invention also accordingly relates to the use of monocarboxylic acid esters of di- and/or triglycerol as the deodorizing principle for cosmetic deodorants.

The invention furthermore relates to a process for combating human body odour caused by microbial decomposition of apocrine perspiration, characterized in that an active amount of monocarboxylic acid esters of di- and/or triglycerol, which can be present in a suitable cosmetic carrier if appropriate, is applied to the skin.

Finally, the invention also relates to the use of monocarboxylic acid esters, in particular monocarboxylic acid monoesters, of di- and/or triglycerol for combating Gram-positive bacteria, in particular coryneform bacteria, and to the use of monocarboxylic acid esters of di- and/or triglycerol for preventing the growth of Gram-positive bacteria, in particular coryneform bacteria.

The cosmetic deodorants according to the invention are particularly advantageously characterized in that the monocarboxylic acid ester or esters of di- and/or triglycerol is or are present in concentrations of 0.01–10.00% by weight, preferably 0.05–5.00% by weight, particularly preferably 0.1–3.00% by weight, in each case based on the total weight of the composition.

The cosmetic deodorants according to the invention can be in the form of aerosols, that is to say preparations which can be sprayed from aerosol containers, squeeze bottles or by means of a pump device, or in the form of liquid compositions which can be applied by means of roll-on devices, in the form of deodorant sticks and in the form of W/O or O/W emulsions, for example creams or lotions, which can be applied from normal bottles and containers. The cosmetic deodorants furthermore can advantageously be in the form of deodorizing tinctures, deodorizing intimate cleansing compositions, deodorizing shampoos, deodorizing shower or bath formulations, deodorizing powders or deodorizing powder sprays.

In addition to water, ethanol and isopropanol, glycerol and propylene glycol, customary cosmetic carriers which can be employed for preparation of the deodorizing formulations according to the invention are skin-care fat or fat-like substances, such as decyl oleate, cetyl alcohol, cetyl stearyl alcohol and 2-octyl-dodecanol, in the ratios of amounts customary for such preparations, as well as mucilagenous substances and thickeners, for example hydroxyethyl- or hydroxypropylcellulose, polyacrylic acid, polyvinylpyrrolidone, and in addition also small amounts of cyclic silicone oils (polydimethylsiloxanes), as well as liquid polymethylphenylsiloxanes of low viscosity, Suitable propellants for cosmetic deodorants according to the invention which can be sprayed from aerosol containers are the customary known readily volatile liquified propellants, for example hydrocarbons (propane, butane or isobutane), which can be employed by themselves or as a mixture with one another. Compressed air can also advantageously be used.

The expert of course knows that there are propellant gases which are non-toxic per se and would be suitable in principle for the present invention, but which should nevertheless be dispensed with because of an unacceptable action on the environment or other concomitant circumstances, in particular fluorochlorohydrocarbons (CFCs).

Emulsifiers, which can be used in the formulations in a small amount, for example 2 to 5% by weight, based on the total composition, and which have proved suitable for the preparation of the cosmetic deodorants according to the invention which are advantageously to be applied to the desired areas of skin as liquid formulations by means of a roll-on device, are nonionic types, such as polyoxyethylene fatty alcohol ethers, for example cetostearyl alcohol polyethylene glycol ether having 12 or 20 added-on ethylene oxide units per molecule, cetostearyl alcohol and sorbitan esters and sorbitan ester-ethylene oxide compounds (for example sorbitan monostearate and polyoxyethylene sorbitan monostearate), and long-chain higher molecular weight waxy polyglycol ethers.

In addition to the constituents mentioned, perfume, dyestuffs, antioxidants (for example α-toco-pherol and its derivatives or butylated hydroxytoluene (BHT=2,6-di-tert-butyl-4-methylphenol) in amounts of 0.01 to 0.03%, based on the total composition), suspending agents, buffer mixtures or other customary cosmetic bases can be admixed to the deodorizing cosmetic formulations according to the invention, the pH of which is preferably brought to 4.0 to 9.0, in particular 5.0 to 6.5, for example by customary buffer mixtures.

The pH of the formulations according to the invention is advantageously brought into the weakly acid to weakly alkaline range, preferably from 4.0 to 9.0, particularly preferably from 5.0 to 6.5.

The particular amounts of cosmetic carrier substances and perfume to be employed can easily be determined by the expert by simple trial and error according to the nature of the particular product.

If appropriate, those substances and perfume oils which are stable, do not irritate the skin and already have antibacterial or bacteriostatic properties as such are also suitable for perfuming.

The cosmetic formulations are prepared in the customary manner, apart from specific formulations which are in each case noted separately in the examples, usually by simple mixing with stirring, if appropriate with gentle heating. The preparation presents no difficulties. For emulsions, the fat phase and the aqueous phase, for example, are prepared separately, if appropriate with heating, and then emulsified.

The customary rules for composition of cosmetic formulations, with which the expert is familiar, are otherwise to be observed.

If the esters according to the invention are to be incorporated into powder sprays, the suspension bases for this can advantageously be chosen from the group consisting of silicic acid gels (for example those which are obtainable under the trade name Aerosil®), kieselguhr, talc, modified starch, titanium dioxide, silk powder, nylon powder, polyethylene powder and related substances.

Advantageous embodiments of the present invention follow.

Example 1

| Aerosol spray I | % by weight |
| --- | --- |
| (a) Liquid phase | |
| Octyldodecanol | 0.50 |
| DMC | 0.50 |
| Perfume | q.s. |
| Ethyl alcohol | to 100.00 |

(b) The liquid phase obtained under (a) is transferred to aerosol containers together with a propane/butane 2.7 mixture in a ratio of 39:61.

Example 2

| Aerosol spray II | % by weight |
| --- | --- |
| (a) Liquid phase | |
| Octyldodecanol | 0.50 |
| DMC | 0.20 |
| Perfume | q.s. |
| Isopropyl alcohol | to 100.00 |

(b) The liquid phase obtained under (a) is transferred to aerosol containers together with a propane/butane 2.7 mixture in a ratio of 39:61.

Example 3

| Pump spray I | % by weight |
| --- | --- |
| (a) | |
| Ethyl alcohol | 60.00 |
| Glycerol | 1.00 |
| PEG 40-hydrogenated castor oil | 2.00 |
| DMC | 0.50 |
| Perfume | q.s. |
| (b) | |
| Water | to 100.00 |

The constituents mentioned under (a) are processed to a homogeneous solution and the solution is then slowly topped up with the aqueous phase (b). The finished pump spray can then be transferred to pump atomizers.

Example 4

| Roll-on gel I | % by weight |
|---|---|
| (a) | |
| 1,3-Butylene glycol | 2.00 |
| Hydroxyethylcellulose | 0.50 |
| (for example Tylose 4000, Hoechst) | |
| (b) | |
| Ethyl alcohol | 60.00 |
| PEG 40-hydrogenated castor oil | 2.00 |
| DMC | 0.30 |
| Perfume | q.s. |
| (c) | |
| Water | to 100.00 |

The constituents mentioned under (a) are dispersed, water (c) is added, the mixture is left to swell at room temperature, and after about 15 minutes a solution of the constituents mentioned under (b) is added. The resulting mixture is homogenized and can be transferred to containers.

Example 5

| Wax stick I | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| DMC | 0.40 |
| Perfume | q.s. |
| Octyldodecanol | to 100.00 |

The constituents are melted at about 75° C. and mixed thoroughly, and the mixture is poured into suitable moulds.

Example 6

| Roll-on emulsion I | % by weight |
|---|---|
| (a) | |
| Triceteareth phosphate | 0.30 |
| Octyldodecanol | 2.00 |
| $C_{12-15}$-alcohol benzoates | 2.00 |
| DMC | 0.50 |
| $C_{10-30}$-alkyl acrylates | 0.15 |
| (b) | |
| Ethyl alcohol | 10.00 |
| Perfume | q.s. |
| (c) | |
| NaOH | 0.05 |
| Water | to 100.00 |

The constituents mentioned under (a) and (c) are in each case heated to 75° C., while stirring. Constituents (a) are then added to (c). The mixture is cooled to 35° C. A solution is prepared from constituents (b), heated to 35° C. and added, with stirring, to the mixture of (a) and (c).

Example 7

| Aerosol spray IV | % by weight |
|---|---|
| (a) Liquid phase | |
| Octyldodecanol | 0.50 |
| TML | 0.20 |
| Perfume | q.s. |
| Isopropyl alcohol | to 100.00 |

(b) The liquid phase obtained under (a) is transferred to aerosol containers together with a propane/butane 2.7 mixture in a ratio of 39:61.

Example 8

| Pump spray II | % by weight |
|---|---|
| (a) | |
| Ethyl alcohol | 60.00 |
| Glycerol | 1.00 |
| PEG 40-hydrogenated castor oil | 2.00 |
| TML | 0.50 |
| Perfume | q.s. |
| (b) | |
| Water | to 100.00 |

The constituents mentioned under (a) are processed to a homogeneous solution and the solution is then slowly topped up with the aqueous phase (b). The finished pump spray can then be transferred to pump atomizers.

Example 9

| Roll-on gel II | % by weight |
|---|---|
| (a) | |
| 1,3-Butylene glycol | 2.00 |
| Hydroxyethylcellulose | 0.50 |
| (for example Tylose 4000, Hoechst) | |
| (b) | |
| Ethyl alcohol | 60.00 |
| PEG 40-hydrogenated castor oil | 2.00 |
| TML | 0.30 |
| Perfume | q.s. |
| (c) | |
| Water | to 100.00 |

The constituents mentioned under (a) are dispersed, water (c) is added, the mixture is left to swell at room temperature, and after about 15 minutes a solution of the constituents mentioned under (b) is added. The resulting mixture is homogenized and can be transferred to containers.

Example 10

| Wax stick II | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| TML | 0.40 |
| Perfume | q.s. |
| Octyldodecanol | to 100.00 |

The constituents are melted at about 75° C. mixed thoroughly, and the mixture is poured into suitable moulds.

Example 11

| Roll-on emulsion II | % by weight |
|---|---|
| (a) | |
| Triceteareth phosphate | 0.30 |
| Octyldodecanol | 2.00 |
| $C_{12-15}$-alcohol benzoates | 2.00 |
| TML | 0.50 |
| $C_{10-30}$-alkyl acrylates | 0.15 |
| (b) | |
| Ethyl alcohol | 10.00 |
| Perfume | q.s. |
| (c) | |
| NaOH | 0.05 |
| Water | to 100.00 |

The constituents mentioned under (a) and (c) are in each case heated to 75° C., while stirring. Constituents (a) are then added to (c). The mixture is cooled to 35° C. A solution is prepared from constituents (b), heated to 35° C. and added, with stirring, to the mixture of (a) and (c).

Example 12

| Pump spray III | % by weight |
|---|---|
| (a) | |
| Ethyl alcohol | 60.00 |
| Glycerol | 1.00 |
| PEG 40-hydrogenated castor oil | 2.00 |
| DML | 0.50 |
| Perfume | q.s. |
| (b) | |
| Water | to 100.00 |

The constituents mentioned under (a) are processed to a homogeneous solution and the solution is then slowly topped up with the aqueous phase (b). The finished pump spray can then be transferred to pump atomizers.

Example 13

| Roll-on gel III | % by weight |
|---|---|
| (a) | |
| 1,3-Butylene glycol | 2.00 |
| Hydroxyethylcellulose | 0.50 |
| (for example Tylose 4000, Hoechst) | |
| (b) | |
| Ethyl alcohol | 60.00 |
| PEG 40-hydrogenated castor oil | 2.00 |
| DML | 0.30 |
| Perfume | q.s. |
| (c) | |
| Water | to 100.00 |

The constituents mentioned under (a) are dispersed, water (c) is added, the mixture is left to swell at room temperature, and after about 15 minutes a solution of the constituents mentioned under (b) is added. The resulting mixture is homogenized and can be transferred to containers.

Example 14

| Wax stick III | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| DML | 0.40 |
| Perfume | q.s. |
| Octyldodecanol | to 100.00 |

The constituents are melted at about 75° C. and mixed thoroughly, and the mixture is poured into suitable moulds.

Example 15

| Roll-on emulsion III | % by weight |
|---|---|
| (a) | |
| Triceteareth phosphate | 0.30 |
| Octyldodecanol | 2.00 |
| $C_{12-15}$-alcohol benzoates | 2.00 |
| DML | 0.50 |
| $C_{10-30}$-alkyl acrylates | 0.15 |
| (b) | |
| Ethyl alcohol | 10.00 |
| Perfume | q.s. |
| (c) | |
| NaOH | 0.05 |
| Water | to 100.00 |

The constituents mentioned under (a) and (c) are in each case heated to 75° C., while stirring. Constituents (a) are then added to (c). The mixture is cooled to 35° C. A solution is prepared from constituents (b), heated to 35° C. and added, with stirring, to the mixture of (a) and (c).

Example 16

| Pump spray IV | % by weight |
|---|---|
| (a) | |
| Ethyl alcohol | 60.00 |
| Glycerol | 1.00 |
| PEG 40-hydrogenated castor oil | 2.00 |
| DMC | 0.20 |
| TML | 0.30 |
| Perfume | q.s. |
| (b) | |
| Water | to 100.00 |

The constituents mentioned under (a) are processed to a homogeneous solution and the solution is then slowly topped up with the aqueous phase (b). The finished pump spray can then be transferred to pump atomizers.

The experiment described below is intended to demonstrate the superiority of the monocarboxylic acid esters according to the invention.

Experiment:
Test organism: Corynebacterium xerosis
Solutions employed:
AC medium: 37 g of brain heart infusion, 5 g of glucose, 1 ml of Tween 80, $H_2O$ to 1 l
Test substance 1: glycerol monolaurate (GML) (comparison substance according to the prior art)
Test substance 2: diglycerol monocaprate (DMC)
Control: AC medium without active compound Test solutions: 4 mmol of the particular test substance in AC medium 50 ml of AC medium were inoculated with 0.2 ml of a fresh overnight culture of the test organism Corynebacteriumxeresis (C. xerosis). The culture vessel was shaken at 30° C. at 250 rpm until a cell density of $10^5$ to $10^6$ cells/ml was reached.

The test substances were weighed out, 5 ml of AC medium were added and the substances were dissolved by heating at 60° C. for about 10 minutes.

The test solutions thus obtained were then added to 5 ml aliquots of the bacterial suspension, samples were taken at various times, while maintaining the growth conditions, and the bacterial titre of the samples was determined by plating out dilutions on nutrient media.

The growth curves for the experimental batches described above are plotted in the graph. In the graph
—o—: Test solution 1
—*—: Test solution 2
—+—: Control (AC medium free from active compound)

We claim:

1. A method of combatting Gram-positive bacteria, which comprises applying to such bacteria or to a locus from which it is desired to exclude such bacteria an amount effective therefor of at least one monocarboxylic acid ester of di or triglycerol.

2. A method of combating human body odor caused by microbial decomposition of apocrine perspiration, wherein an active amount of monocarboxylic acid esters of di- and/or triglycerol, optionally in a suitable cosmetic carrier is applied to the skin.

3. The method according to claim 1, wherein the diglycerol is esterified with carboxylic acids in the 1-position or the triglycerol is esterified with carboxylic acids in the 2'-position.

4. The method according to claim 3, wherein the diglycerol is esterified with carboxylic acids in the 1-position or the triglycerol is esterified with carboxylic acids in the 2'-position.

5. A method according to claim 2, wherein the monocarboxylic acid esters of diglycerol are monocarboxylic acid monoesters having the following structures:

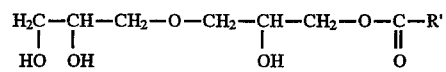

wherein R' is a hydrocarbon radical, advantageously a branched or unbranched alkyl or alkenyl radical having 5 to 17C atoms.

6. Method according to claim 5, wherein the monocarboxylic acid esters of triglycerol are monocarboxylic acid monoesters having the following structures:

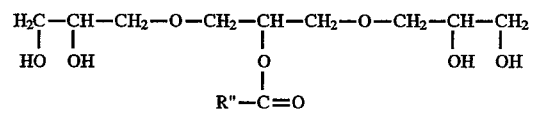

wherein R" is a hydrocarbon radical, advantageously a branched or unbranched alkyl or alkenyl radical having 5 to 17C atoms.

7. Method according to claim 5, wherein R' is chosen from the group consisting of
diglycerol monocaprate (DMC) R'=9
triglycerol monolaurate (TML) R"=11
diglycerol monolaurate (DML) R'=11, and
triglycerol monomyristate (TMM) R'=13.

8. Method according to claim 5, wherein R" is chosen from the group consisting of
diglycerol monocaprate (DMC) R'=9
triglycerol monolaurate (TML) R"=11
diglycerol monolaurate (DML) R'=11, and
triglycerol monomyristate (TMM) R'=13.

9. Method according to claim 2, wherein the monocarboxylic acid ester or esters of di- and/or triglycerol is or are present in concentrations of 0.01–10.00% by weight, based on the total weight of the composition.

10. In a cosmetic deodorant comprising a deodorant base and a deodorant, the improvement wherein such deodorant comprises at least one monocarboxylic acid ester of di- or triglycerol.

11. A cosmetic deodorant according to claim 10, wherein the ester is present in about 0.01–10.00% by weight.

* * * * *